United States Patent
Ipsen et al.

(10) Patent No.: US 12,193,696 B2
(45) Date of Patent: Jan. 14, 2025

(54) TRANSPORTER WITH LOCKING DEVICE

(71) Applicant: OLYMPUS WINTER & IBE GMBH, Hamburg (DE)

(72) Inventors: Hendrik Ipsen, Barsbüttel (DE); Christian Brockmann, Hollenstedt (DE); Hannes Miersch, Hamburg (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 1011 days.

(21) Appl. No.: 17/100,426

(22) Filed: Nov. 20, 2020

(65) Prior Publication Data
US 2021/0161550 A1 Jun. 3, 2021

(30) Foreign Application Priority Data

Nov. 29, 2019 (DE) ...................... 10 2019 132 536.6

(51) Int. Cl.
*A61B 17/32* (2006.01)
*A61B 1/307* (2006.01)
(Continued)

(52) U.S. Cl.
CPC ...... *A61B 17/320016* (2013.01); *A61B 1/307* (2013.01); *A61B 18/1485* (2013.01);
(Continued)

(58) Field of Classification Search
CPC ... A61B 18/1485; A61B 18/149; A61B 18/12; A61B 18/14; A61B 2018/00517; A61B 2018/00982; A61B 2018/1407; A61B 2018/00601; A61B 2018/0097; A61B 2018/00053; A61B 17/320016; A61B 1/307; A61B 1/121; A61B 1/0014;
(Continued)

(56) References Cited

U.S. PATENT DOCUMENTS

| 4,648,399 A | 3/1987 | Nakada |
| 4,955,884 A * | 9/1990 | Grossi ................ A61B 18/1485 606/46 |

(Continued)

FOREIGN PATENT DOCUMENTS

| DE | 3500527 A1 | 7/1985 |
| DE | 102010019781 A1 | 11/2011 |

(Continued)

*Primary Examiner* — Khadijeh A Vahdat
*Assistant Examiner* — Marina Delaney Templeton
(74) *Attorney, Agent, or Firm* — Oliff PLC

(57) ABSTRACT

A transporter for a resectoscope for endoscopic surgery, wherein the transporter has a connection body and, for connection to a system component in the connection body, a latch system including an elongate latch element, which is arranged transversely with respect to the longitudinal axis of the transporter and has an engagement opening or an engagement groove, and a spring element, wherein one or more irrigation channels, arranged parallel to the longitudinal axis of the latch element, are formed between latch element and connection body. The invention further relates to a resectoscope for use in endoscopic surgery, wherein it includes a transporter according to one of the preceding claims and preferably a system component latched in the transporter.

8 Claims, 4 Drawing Sheets

(51) Int. Cl.
*A61B 17/00* (2006.01)
*A61B 18/00* (2006.01)
*A61B 18/14* (2006.01)

(52) U.S. Cl.
CPC .. *A61B 18/149* (2013.01); *A61B 2017/00137* (2013.01); *A61B 2018/00517* (2013.01); *A61B 2018/00982* (2013.01); *A61B 2018/1407* (2013.01); *A61B 2217/007* (2013.01); *A61B 2218/002* (2013.01)

(58) Field of Classification Search
CPC ......... A61B 1/123; A61B 1/125; A61B 1/126; A61B 1/12; A61B 1/00133; A61B 1/018; A61B 2217/007; A61B 2218/002; A61B 90/70; A61B 2090/0813; A61B 2017/0046; A61B 2017/2931; A61B 2017/00137
See application file for complete search history.

(56) References Cited

U.S. PATENT DOCUMENTS

| | | | |
|---|---|---|---|
| 6,039,752 A * | 3/2000 | Kimura | A61B 17/2909 |
| | | | 606/205 |
| 6,358,200 B1 | 3/2002 | Grossi | |
| 6,358,267 B1 * | 3/2002 | Murakami | A61B 17/29 |
| | | | 606/205 |
| 2004/0242959 A1 | 12/2004 | Nosel | |
| 2005/0010080 A1 * | 1/2005 | Dickopp | A61B 18/149 |
| | | | 600/105 |
| 2008/0224427 A1 | 9/2008 | Schwarz et al. | |
| 2015/0351826 A1 | 12/2015 | Kroeber et al. | |
| 2016/0193012 A1 * | 7/2016 | Anderson | A61B 1/015 |
| | | | 606/130 |

FOREIGN PATENT DOCUMENTS

| | | |
|---|---|---|
| DE | 102011011216 A1 | 8/2012 |
| DE | 102013001156 A1 | 7/2014 |
| DE | 102011121792 B4 | 7/2015 |
| DE | 102015010877 A1 | 3/2017 |
| JP | 2003-175047 A | 6/2003 |

* cited by examiner

TRANSPORTER WITH LOCKING DEVICE

BACKGROUND

The invention relates to a transporter of the type set out in the preamble of Claim 1.

Transporters of the type in question are used in resectoscopes, particularly in urology when performing surgical work in the bladder and the urethra. They are used, for example, in conjunction with electrosurgical passage instruments for resection and vaporization of tissue, for example of tissue in the lower urinary tract. For this purpose, the resectoscopes comprise a longitudinally displaceable electrode instrument which, after the insertion of the resectoscope, can be advanced with its distal working end out of the distal end of the shaft tube of the resectoscope.

At its proximal end, the electrode instrument is connected to the transporter of the resectoscope, by which it can be displaced in the longitudinal direction in order to execute the cutting movement. The transporter is usually fastened removably on the proximal end of the shaft tube of the resectoscope.

The transporter has a longitudinally displaceable carriage, to which the electrode instrument can be coupled for joint longitudinal movement. The transporter is usually actuated by the fingers of one hand, which fingers engage on the carriage and on the stationary parts of the transporter that are rigidly connected to the guide tube. The movement of the transporter can in this case take place, for example, counter to a restoring spring, which can be designed as a leg spring or leaf spring. Examples of instruments are described in DE 10 2011 011 216 A1, US 2004/0242959 A1, U.S. Pat. No. 6,358,200 and DE 35 00 527 A1.

The coupling between the transporter and work instruments that can be longitudinally displaced by the latter, for example an electrode instrument, or other stationary system components, such as the shaft, is usually effected via latching connections. For example, when the proximal end of the electrode instrument is brought into contact with the corresponding connection partner in the transporter, the insertion of the electrode instrument generally effects an automatic latching of the instrument. By contrast, the unlatching of the electrode instrument usually has to be assisted manually.

The latching of the electrode instrument is at present effected by an undercut of an elongate latch element in a groove provided for this purpose in the instrument shaft. The latch element is for this purpose arranged transversely with respect to the longitudinal direction of the work instrument and of the resectoscope shaft in the transporter. By means of an insertion bevel on the latch element, the shaft of the inserted work instrument generates a force which displaces the latch element along its own longitudinal axis and transversely with respect to the longitudinal axis of the work instrument. By means of a counter-pressure exerted by a spring element, the latch element is then pressed back to its starting position and the undercut in the latching connection is ensured. The spring element used in the latching connection can be, for example, a compression spring or a shaped elastomer part.

In order to ensure a defined rest position of the latch element, even without a latched-in work instrument, and to prevent undesired dismantling, the latching connection usually comprises a built-in blocking element which is set into an aperture of the latch element and prevents the latch system from undesirably falling out of the transporter.

The unlatching of the work instrument or of the other latched system components is effected by the operating personnel manually displacing the latch element transversely with respect to the longitudinal axis of the transporter.

Since the latch element is arranged movably in a channel inside a connection body of the transporter, a narrow gap is present around the latch element, and this narrow gap can be accessed only with difficulty during cleaning and sterilization. Moreover, the displacements of the latch element can lead to smears of dirt in this gap. In addition, the channel in which the latch element is arranged inside the connection body is often closed on both sides of the transporter. On one side, the channel is closed by a side wall of the transporter, and on the other side it is closed by the spring element, for example in the form of a shaped elastomer part, or an actuation element. This additionally makes cleaning difficult and creates further cavities that are difficult to clean. It is also possible for dirt to gather in the aperture that is provided in the latch element for the blocking element. Moreover, the use of a shaped elastomer part as spring element entails the risk that, as a result of the deformation that occurs upon actuation of the latch element, dirt may become trapped in the spring element at places that are difficult to clean or that cannot be cleaned at all.

The object of the present invention is therefore to make available a transporter that can be more easily and more reliably cleaned, particularly in the region of the latch system provided for the latching of work instruments and other system components.

DESCRIPTION

This object is achieved by a transporter and by a resectoscope of embodiments described herein.

The invention relates, particularly in a first aspect, to a transporter for a resectoscope for endoscopic surgery, wherein the transporter has a connection body and, for connection to a system component in the connection body, a latch system comprising an elongate latch element, which is arranged preferably transversely with respect to the longitudinal axis of the transporter and has an engagement opening or an engagement groove, and a spring element, characterized in that one or more irrigation channels, arranged parallel to the longitudinal axis of the latch element, are formed between latch element and connection body.

In a preferred embodiment, the invention relates to a transporter for a resectoscope for endoscopic surgery, wherein the transporter is designed to control the longitudinal displacement of a work instrument having an elongate shaft portion and, for connection to the proximal end region of the work instrument, has a latch system comprising an elongate latch element, arranged transversely with respect to the longitudinal axis of the transporter and with a lateral engagement opening, and a spring element, characterized in that the latch element has one or more irrigation grooves arranged parallel to the longitudinal axis of the latch element.

In a related aspect, the invention relates to a resectoscope for use in endoscopic surgery, characterized in that it comprises a transporter according to the invention and preferably a system component latched in the transporter, particularly preferably a work instrument.

By the incorporation, according to the invention, of irrigation grooves into the latch element and/or into the connection body, irrigation channels are formed in the transporter which are accessible from the outside and which facilitate and improve the cleaning and sterilization of the latch system. All the elements of the latch system can be rinsed all around with irrigation liquid during cleaning and/or can be reached by sterilization gas during sterilization. The danger of continuous contamination of the instruments is thus greatly reduced compared to the prior art.

The latch system modified according to the invention is suitable for transporters used in endoscopic surgery. A high degree of cleanness and sterility is particularly important for these instruments. The transporters are generally parts of a resectoscope that additionally usually has a shaft part with a tubular shaft and an elongate optic insertable into the shaft part through the transporter. The parts of the resectoscope may be adapted to the requirements of the particular intervention and therefore vary.

In addition to the transporter, shaft part and optic, the resectoscopes can have further parts, for example an illumination means, such as an optical fibre bundle, and various work instruments (passage instruments) which are guided through the shaft of the resectoscope to the site of the intervention and which can be used there for manipulation of tissue, for example.

The transporter has a connection body in which the latch system according to the invention is arranged. The connection body thus directly adjoins the latch system, in particular the latch element of the latch system, but also the other components of the latch system. If the transporter is to be designed for longitudinal displacement of the latched system component, the connection body can be the carriage of the transporter, for example, or a part of the carriage.

The transporter is designed by means of the latch system for connection to a system component. Preferably, the connection body in particular of the transporter is designed for connection to a system component. This means that the system component can be held releasably by the latch system in the transporter, particularly in the connection body thereof.

The latch system is suitable for the latching of different parts. The system component can therefore be any component (part) of a resectoscope that is intended to be connected releasably to the transporter, in particular to the connection body thereof. The system component is not then part of the transporter. The system component can be chosen, for example, from the group comprising work instrument (passage instrument), optic, shaft tube system (e.g. outer tube and/or inner tube) and others. In a preferred embodiment, the system component is a work instrument. In another embodiment, the system component is an optic.

It will be appreciated that the transporter according to the invention can comprise not just one latch system as described herein, but also several of them, in which case the various latch systems are each designed and arranged for the latching of different system components. The transporter can comprise, for example, one, two, three or more of the latch systems described herein, preferably two or more.

As has been mentioned, the latchable system component is preferably a work instrument. These are generally arranged in a resectoscope in a longitudinally displaceable manner, so as allow the specialist medical team flexibility at the intervention site. The transporter can accordingly be designed to control the longitudinal displacement of a work instrument. Suitable work instruments that can be used for an intervention in endoscopic surgery are known to specialists in the field. For example, the work instrument can be an electrode instrument or a stone collection instrument, the work instrument described herein preferably being an electrode instrument.

The electrode instrument has an elongate shaft portion (shaft part) and is designed as a passage instrument for a resectoscope, i.e. as an instrument that is insertable into an opening of the body through a resectoscopic shaft tube. At its distal end, the electrode instrument has an electrode to which high-frequency current can be applied. The electrode can be a cutting loop, a vaporization head (PlasmaButton) or other commercially available electrode. The electrode is preferably a cutting-loop electrode. Corresponding electrodes and electrode instruments are known to specialists in the field.

The electrode instrument can be a bipolar electrode instrument, which comprises the electrode as part of an electrode assembly. In this case, the electrode instrument will comprise, for example, a second electrode in the distal end region of the electrode instrument, designed as neutral electrode. Alternatively, the second electrode (neutral electrode) can also be arranged on other elements of the distal end region of the resectoscope. Of course, the electrode instrument can also be designed as a monopolar instrument.

The system component can have an elongate shaft portion. The longitudinal axis of the system component is preferably parallel to the longitudinal axis of the resectoscope shaft or of the transporter. The proximal end region of the system component can be connected to the latch system. However, it is also conceivable to connect, i.e. latch, a lateral face of the system component to an engagement opening or engagement groove arranged laterally on or in the connection body. The latch system is preferably designed, however, for connection to the proximal end region of the system component. In this embodiment, the proximal end region of the system component is insertable into the engagement opening or engagement groove of the latch system.

If the system component is a work instrument, the work instrument can be longitudinally displaceable inside the shaft of the resectoscope by the transporter, i.e. is axially movable in a distal direction and a proximal direction. For attachment to the resectoscope, the work instrument has the elongate shaft portion which, in order to produce a connection that provides coupling in terms of movement, can be latched at its proximal end region on a carriage comprised by the transporter. The carriage typically slides on a tube and is held with pretensioning in a rest position via a spring unit. Thus, the work unit, e.g. the electrode, at the distal end can be moved towards and away from tissue that is to be cut, without the whole resectoscope having to be moved. In addition, by virtue of the longitudinal displaceability of the work instrument, it is possible for example to clamp tissue between a distal electrode and the insulation insert and remove it from the intervention site.

The proximal end region of the shaft portion of the work instrument is connected to the transporter by means of a latch system. The latch system is part of the transporter and is preferably arranged inside the carriage of the transporter. In this way, the work instrument, after it has been latched inside the carriage, can be moved together with the latter.

The latch system of the transporter according to the invention always comprises a latch element and a spring element and, in addition, can optionally comprise a blocking element. The latch system is arranged inside and on the transporter such that the latch element and optionally the blocking element are arranged for the most part, i.e., by about 50% or more, inside the transporter. For this purpose, the transporter has a corresponding channel-shaped hollow (channel). The latter is open at least on one side of the transporter, preferably on both sides. The hollow is more or less complementary in shape and size to the latch system. As has been described above, however, free gaps are present in the edge regions of the latch element, of the spring element and of the blocking element, which free gaps arise in the course of production and/or are necessary for ensuring a free rotatability and displaceability or other functions of the latch system.

The latch element is elongate and arranged transversely with respect to the longitudinal axis of the transporter. The latch element can have a shaft part and, at one end, a head part which has a greater diameter than the shaft part. This head part can serve, for example, to support the spring element. Shaft part and head part preferably have a substantially round cross section, optionally with recesses for the irrigation grooves. In other words, the latch element can have, in its shaft part, a substantially cylindrical shape, optionally with recesses for the irrigation grooves and the blocking groove.

The latch element has in its lateral surface, i.e. laterally in relation to its longitudinal axis, one or more lateral engagement openings and/or one or more lateral engagement grooves. One of the engagement openings or one of the engagement grooves is arranged and suitable for the insertion of one part of the system component, preferably the proximal end region of the work instrument.

The engagement opening can be formed like a channel and have a substantially cylindrical interior. The engagement opening can extend through the shaft part of the latch element like a channel. The engagement opening can thus generate an opening at both sides of the latch element. Alternatively, the engagement opening can be closed at the side opposite the work instrument.

The engagement groove can have a U-shaped cross section or a cross section in the shape of part of a circle and can extend through the shaft part of the latch element. The groove is preferably open at both ends along its longitudinal direction, i.e. allows a gas or a liquid to flow through.

The engagement opening and the engagement groove are arranged transversely with respect to the longitudinal axis of the latch element.

The latch element can have further engagement openings, for example for the engagement of a blocking element. However, according to the invention, it is preferable that a blocking element is arranged in a blocking groove in the outer wall of the latch element, as is described elsewhere herein.

To permit the insertion and automatic latching of the system component, preferably the work instrument, into the latch element, the engagement opening or the engagement groove can have a partially funnel-shaped inlet region, i.e. an inlet region bevelled on one side. The engagement opening or engagement groove is widened in this inlet region. During insertion, the proximal end of the work instrument can slide along a bevel surface of the inlet region and thus move the latch element to the side, i.e. transversely with respect to the longitudinal axis of the transporter, in such a way that the spring element designed as a compression spring is compressed.

The engagement opening or engagement groove provided for the system component, preferably the proximal end region of the work instrument, can additionally comprise one or more latch elements or grooves which enter into a latching connection with a latch element or a groove on the work instrument. In this way, a suitable undercut in the latching connection can be ensured.

One or more irrigation channels arranged parallel to the longitudinal axis of the latch element are formed according to the invention between latch element and connection body. The irrigation channels can be formed either by the formation of irrigation grooves in the outer wall of the latch element or by formation of irrigation grooves in the inner face of the connection body adjoining the latch element. A combination of irrigation grooves on both parts is also conceivable and is possible within the scope of the invention. Thus, in one embodiment, the latch element has one or more irrigation grooves arranged parallel to the longitudinal axis of the latch element. Alternatively or in addition, the connection body can have one or more irrigation grooves arranged parallel to the longitudinal axis of the latch element and preferably adjoining the latch element. Within the scope of the invention, it is also conceivable to form irrigation grooves in both parts, in such a way that an irrigation groove of the latch element in each case adjoins an irrigation groove of the connection body.

The irrigation grooves can each have a cross section in the shape of part of a circle, e.g. a hemispherical cross section, or a U-shaped cross section. The irrigation grooves are suitable for generating a liquid channel via which liquid can be flushed through gaps present between the latch element and the other parts of the transporter. For this purpose, the irrigation grooves are preferably open at both ends of the elongate latch element or of the adjoining connection body, in order to allow irrigation liquid to flow in and out. The two ends of the latch element are the ends lying along the longitudinal axis of the latch element. Inside the transporter, these ends are oriented towards the sides of the transporter (laterally). Irrigation liquid and/or gas (sterilizing gas) can accordingly be conveyed through the irrigation grooves from a lateral face of the transporter to the contralateral face of the transporter.

The latch element or the connection body can have one or more irrigation grooves, i.e. for example one, two, three, four or more irrigation grooves. In a preferred embodiment, the latch element or the connection body, preferably the latch element, has four irrigation grooves. The irrigation grooves can be distributed about the longitudinal axis of the latch element, on its circumference, or on the inner circumference of the hollow space of the connection body. All the irrigation grooves are preferably spaced apart equidistantly from one another. Thus, in a latch element or connection body with four irrigation grooves, the grooves can be arranged at 0°, 90°, 180° and 270° on the circumference thereof or on the inner circumference of the hollow. Pairs of irrigation grooves lying opposite each other are preferably arranged on the latch element or on the inner circumference of the hollow.

The latch system can moreover comprise an elongate blocking element which is arranged, transversely with respect to the longitudinal axis of the latch element, in a blocking groove in the outer wall of the latch element. In the absence of the work instrument, the blocking element prevents the latch system from falling out of the transporter. The blocking element has an elongate shaft of which one end, preferably the proximal end, is arranged at least partially in an opening of the transporter or of the carriage, which opening is not part of the latch element. In other words, this end is arranged in a body of the transporter surrounding the latch system. The other end of the blocking element, preferably the distal end, is arranged in a blocking groove of the latch element. Thus, in the absence of the work instrument, a part of the blocking element bears on a lateral face of the blocking groove and thereby prevents further movement of the latch element in the direction of the spring force exerted by the spring element. The blocking element can comprise a head part which is accessible from outside the connection body and which has a wider diameter.

The blocking groove is arranged laterally in the shaft part of the latch element. The blocking groove is preferably located in the end region of the latch element that does not adjoin the spring element. The blocking groove can have a cross section in the shape of part of a circle. It preferably adjoins one or more irrigation grooves and forms an irrigation channel with the irrigation groove(s). These irrigation channels formed by the irrigation grooves, and optionally by the blocking groove, extend preferably over the entire length of the latch element.

The blocking groove is at least in part designed with a shape and size complementary to the blocking element. However, in the longitudinal direction of the latch element, the blocking groove has a diameter greater than the width of the blocking element, in order to ensure a desired displaceability of the latch element in the longitudinal direction of the latch element.

The latch system moreover comprises a spring element. The spring element exerts a spring force in the direction of an outer side of the transporter, for example the outer side facing away from a blocking element. When the shaft of the work instrument is inserted into the engagement opening, a pressure is thereby exerted on the shaft in order to secure the undercut (clamping action). The spring element is preferably a compression spring, for example a helical compression spring, or an elastic shaped part. In preferred embodiments, the spring element is a helical compression spring. Since the latter does not create additional cavities in the latch system, the latch system thus obtained can be cleaned more easily and more reliably. It is particularly preferable that the spring element, in particular the helical compression spring, is made of metal. Suitable spring elements are known to specialists in the field.

BRIEF DESCRIPTION OF THE FIGURES

Illustrative embodiments of the invention are shown schematically in the drawings, in which.

ILLUSTRATIVE EMBODIMENTS

Further advantages, characteristics and features of the present invention will become clear from the following detailed description of illustrative embodiments in which reference is made to the accompanying drawings. However, the invention is not limited to these illustrative embodiments.

Figure 1:
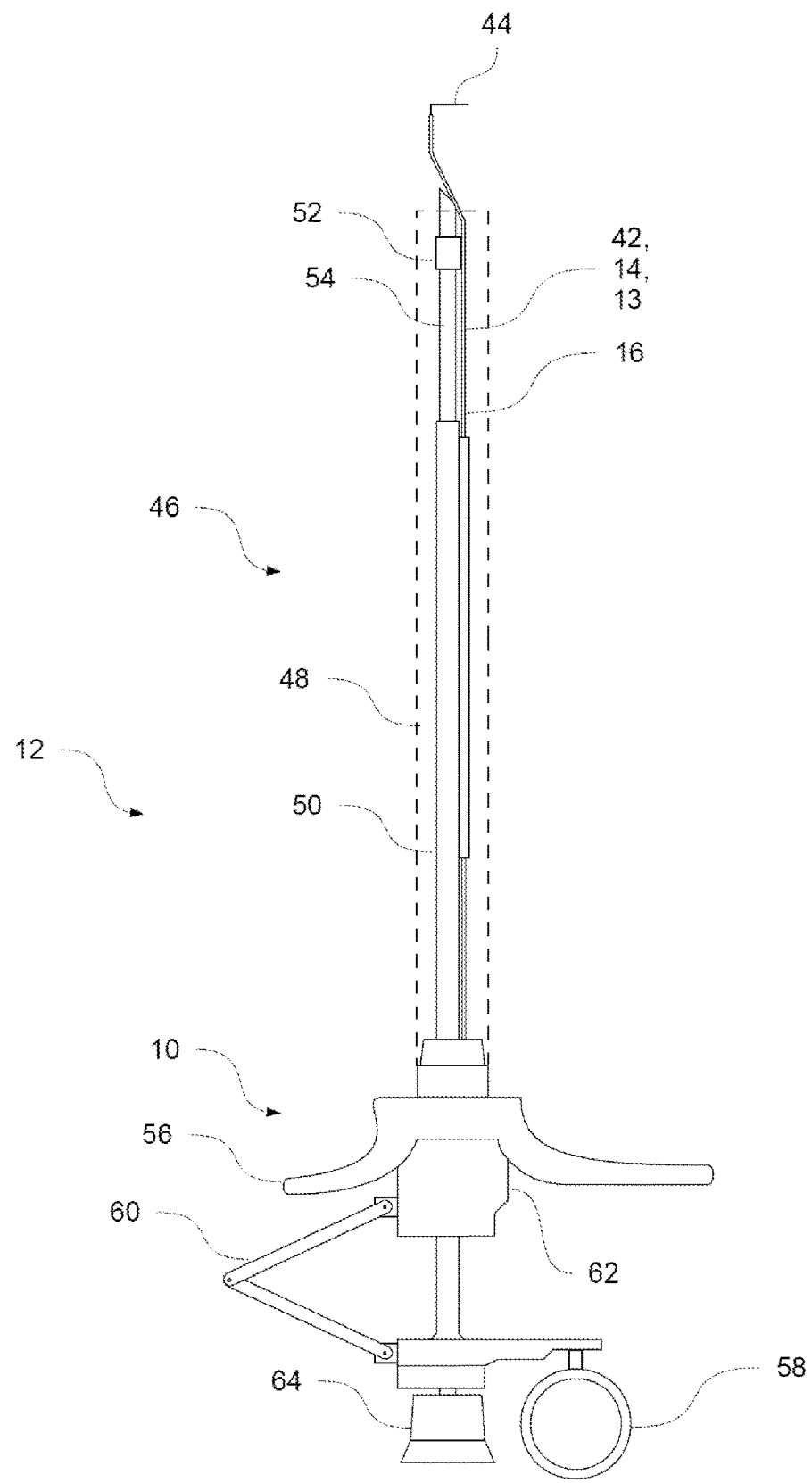
FIG. 1 shows a lateral, schematic sectional view of a resectoscope according to the invention, which has a transporter and an electrode instrument, the latter being longitudinally displaceable by means of the carriage of the transporter.

FIG. 1 shows a lateral, schematic sectional view of a resectoscope 12 according to the invention, which has a transporter 10 and an electrode instrument 42, the latter being longitudinally displaceable by means of the carriage 62 of the transporter 10. The electrode instrument 42 is the system component 13 of the transporter 10 that is intended to be held releasably on the transporter 10 by means of a latch system 18.

The resectoscope 12 has a shaft 46 comprising a shaft tube system 48, which is indicated by hatching and which, in a manner not shown, consists of an outer tube and an inner tube. Extending inside the shaft tube system 48 is an optics guide tube 50 and, inside the optics guide tube 50, an optic 54. Extending between optics guide tube 50 and shaft tube system 48 is a work instrument 14, which is designed as an electrode instrument 42. In addition, an illumination means, for example in the form of an optical fibre bundle, extends in the inside of or outside the optics guide tube 50. In addition, further elements not shown here may extend in the resectoscope 12, for example a separate irrigation tube and the like. In its distal end region, the shaft tube system 48 comprises, in a manner not shown here, openings through which contaminated irrigation liquid can flow into the space between outer tube and inner tube and can drain off through the resectoscope shaft 46.

By means of a guide element 52, which has a cross section in the shape of part of a circle, the electrode instrument 42 is protected against displacements that deviate from the longitudinal direction of the shaft 46, for example transversely with respect to the longitudinal direction. The guide element 52 is supported on the optic 54. The electrode instrument 42 is mounted longitudinally displaceably on the optics guide tube 50 and has an elongate shaft 16.

The proximal end of the shaft 16 of the electrode instrument 42 is latched in the interior of the carriage 62 of the transporter 10 in a manner not shown in FIG. 1. The carriage 62 can thus be regarded as connection body 15 in the embodiment shown. By actuation of the grip parts 56, 58, the electrode instrument 42 can be moved in a constrained axial movement in the distal and proximal direction. It can be pushed beyond the distal end of the optics guide tube 50 and of the shaft tube system 48. The operator is thus also able to manipulate tissue that is located further away from the resectoscope tip. At its distal end, the electrode instrument 42 has an electrode 44, which is designed as a cutting loop and by means of which tissue can be removed by electrosurgical ablation. A high-frequency electrical voltage is applied to the electrode 44 in order to cut tissue.

The resectoscope 12 shown has a passive transporter 10 in which, by relative movement of the grip parts 56 and 58 arranged proximally from the resectoscope shaft 46, the carriage 62 is displaced in the distal direction towards the distal, first grip part 56 counter to a spring force applied by a spring bridge 60. In the displacement of the carriage 62 in the distal direction towards the grip part 56, the electrode instrument 42 is forced in the distal direction by the latching (not shown in FIG. 1) in the latch system 18. Upon relaxation of the grip parts 58, 56, the spring force generated by the spring bridge 60 forces the carriage 62 back to its rest position, wherein the electrode instrument 42 is pulled in the proximal direction. Upon the rearward displacement of the carriage 62, an electrosurgical intervention can be performed with the electrode instrument 42 without manual force from the operator, i.e. passively.

Figure 2:
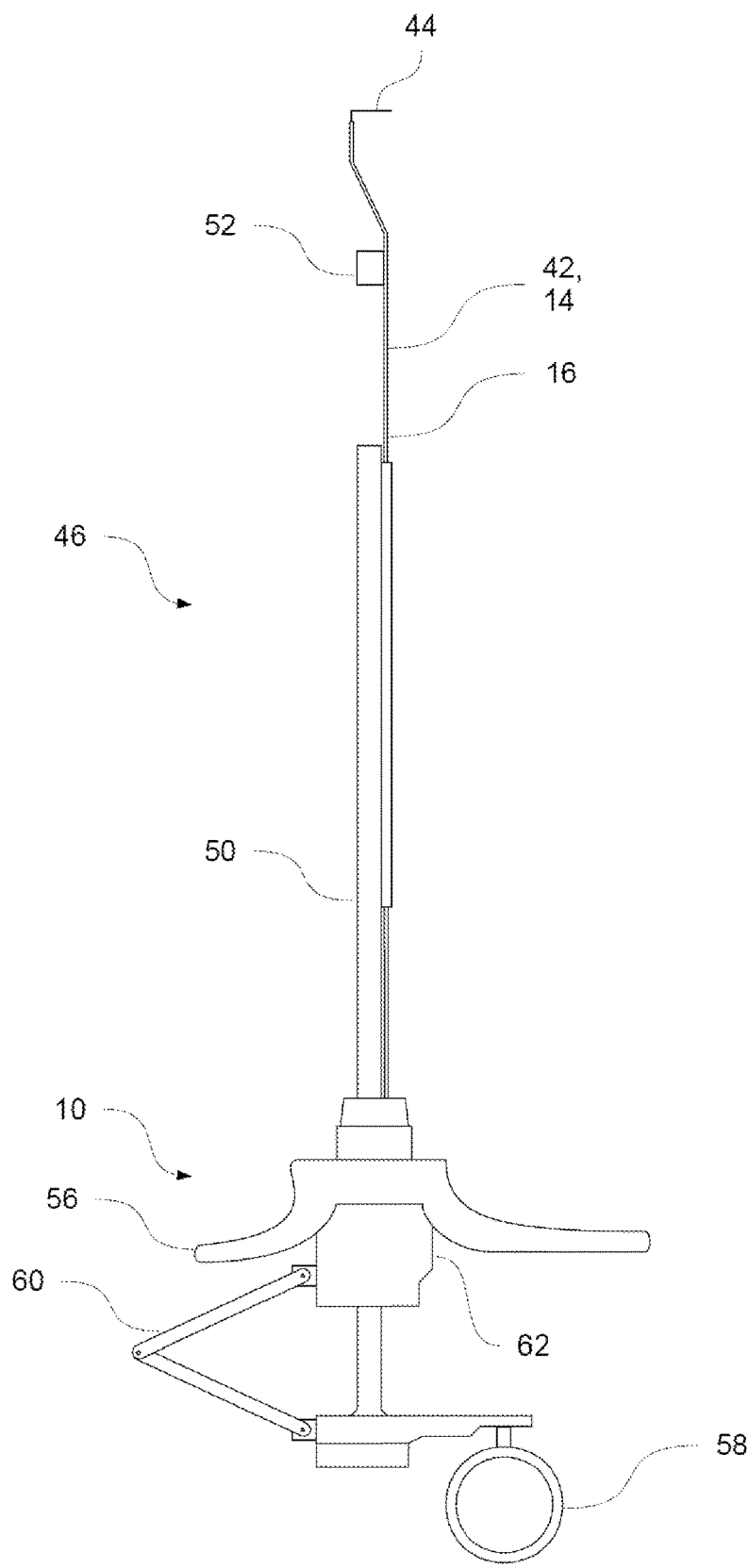
FIG. 2 shows a lateral, schematic sectional view of a transporter according to the invention, with an electrode instrument which is longitudinally displaceable by means of the carriage of the transporter.

FIG. 2 shows a lateral, schematic sectional view of the transporter 10 according to the invention shown in FIG. 1, with the electrode instrument 42 longitudinally displaceable by means of the carriage 62 of the transporter 10, and with the optics guide tube 50, but without the shaft tube system 48 of the resectoscope 12 and without the optic 54. It will be seen that the electrode instrument 42 is inserted with the proximal end region of its shaft portion 16 into the carriage 62 of the transporter 10 and is held thereby.

Figure 3:
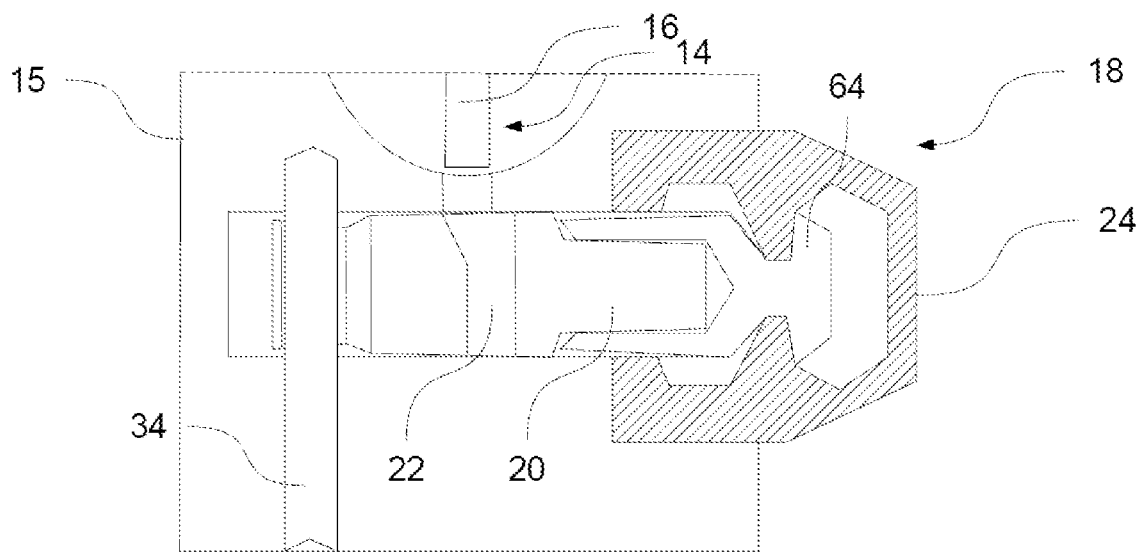
FIG. 3 shows a schematic sectional view of a part of a transporter from the prior art, said transporter having a latch system with a latch element, a spring element and a blocking element, the latch element having no irrigation channels.
Figure 4:
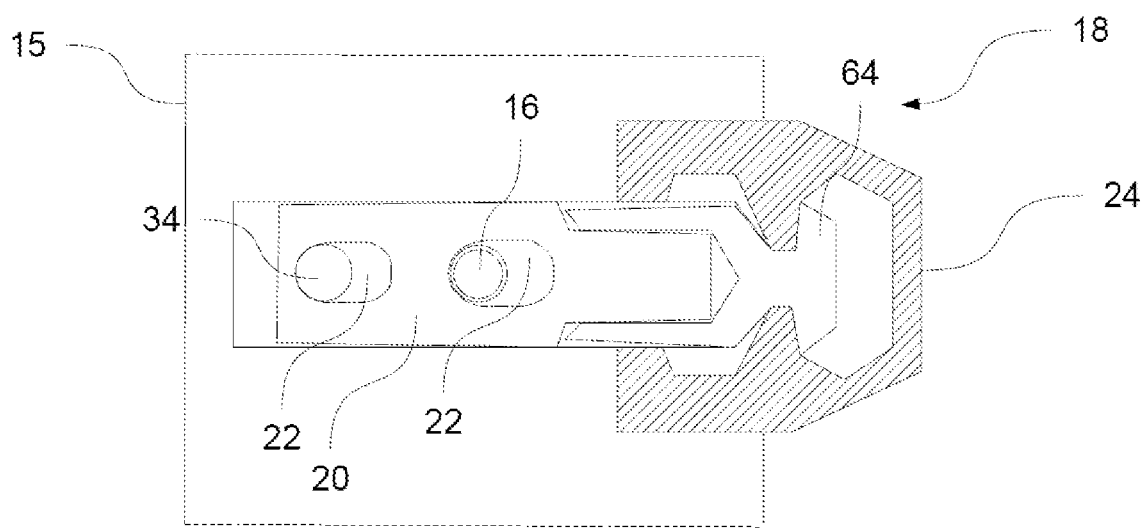
FIG. 4 shows a schematic sectional view of the part from FIG. 3, rotated through 90°.

FIGS. 3 and 4 show schematic sectional views of a part of a transporter 10 from the prior art, which comprises a latch system 18 with a latch element 20, a spring element 24 and a blocking element 34. The transporter 10 from the prior art differs from the transporter 10 according to the invention shown in FIG. 5 mainly in that the latch element 20 of the transporter 10 shown in FIGS. 3 and 4 has no irrigation channels. FIG. 4 shows a schematic sectional view of the part from FIG. 3 rotated through 90°.

The proximal end region of the shaft portion 16 of a work instrument 14 is shown which, in FIG. 3, is located above an engagement opening 22 and has not yet been inserted into the latter and not yet latched in place therein. The end region has a diameter smaller than the diameter of the engagement opening 22. The engagement opening 22 is arranged in the shaft region of the latch element 20 and fully traverses the latter, i.e. is designed in the form of a channel that is open at both ends. By insertion of the shaft portion 16 into the half-funnel-shaped end region of the engagement opening 22, the latch element 20 is displaced along its longitudinal axis in the direction of the blocking element 34 or in the direction of the funnel start (to the left in FIG. 3).

As is described elsewhere herein, the engagement opening 22 and the end region of the shaft portion 16 of the work instrument 14 can have complementary latching lugs and latching grooves (not shown) and can thus form an additional latching connection. Moreover, by means of the spring element 24, a latching lug of the latch system is at all times pressed onto the bottom of the latching groove, i.e. a pressure is exerted on the shaft of the work instrument 14. In this way, the undercut within the latch system 18 is ensured. Seen from the direction of the longitudinal axis of the latch element 20, the spring element 24 is arranged at one end of the latch element 20. The spring element 24 is designed as an elastic shaped body and, in contrast to the latch element 20 and the blocking element 34, is arranged partially outside the transporter 10. The part of the spring element 24 protruding laterally from the side wall of the transporter can be used for manual actuation of the latch element 20, in particular for releasing a latching connection present between the work instrument 14 and the latch system 18. If a (manual) pressure is exerted on the spring element 24, the force is transmitted to the latch element 20, via an optional force transmission element 64, and the latch element 20 is displaced along its longitudinal axis in the interior of the transporter 10. In this way, the clamping and/or latching connection between engagement opening 22 and shaft portion 16 is released, such that the work instrument 14 can be easily removed from the resectoscope 12.

The transporter 10 moreover has a blocking element 34 which is arranged in part in a second engagement opening 22 and in part in a channel (not shown in detail) in the connection body 15. In this way, the latch element 20 is held in the transporter 10, and protected from falling out, even when there is no work instrument 14 arranged in the first engagement opening 22. The blocking element 34 is of elongate shape and is oriented transversely with respect to the longitudinal direction of the latch element 20 and parallel to the longitudinal direction of the transporter 10 and of the shaft 46. The engagement opening 22 provided for the blocking element 34 is preferably designed as a channel substantially parallel to the engagement opening 22 provided for the work instrument 14. Moreover, in the longitudinal direction of the latch element 20, it is wider than the diameter of the blocking element 34, so as not to impede the desired displacement of the latch element 20 in its longitudinal direction. The additional width, i.e. the width beyond the diameter of the blocking element, preferably corresponds to the desired stroke of the latch element 20.

Figure 5:
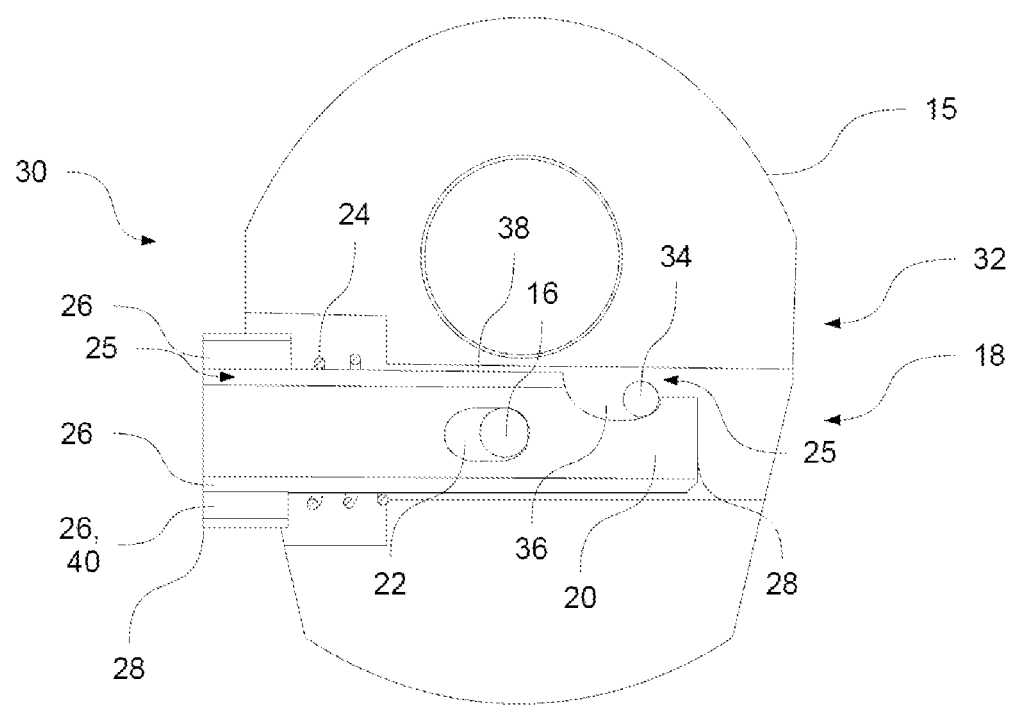
FIG. 5 shows a schematic sectional view of the latch system of a transporter according to the invention, from the longitudinal direction of the transporter, in which the irrigation grooves of the blocking element can be seen.

FIG. 5 shows a schematic sectional view of the latch system 18 of a transporter 10 according to the invention, from the longitudinal direction of the transporter 10, in which the irrigation grooves 26 of the blocking element 34 can be seen. The transporter 10 according to the invention differs from the one shown in FIGS. 3 and 4 at least in terms of the irrigation grooves 26 shown here. Other features, such as the arrangement of the blocking element 34 in an engagement opening 22 or the use of an elastic shaped body as spring element 24, can also be applied in the transporter 10 of the present invention.

The irrigation grooves 26 of the latch element 20 extend parallel to the longitudinal axis of the latch element 20, from one end of the latch element 20 to the other. This ensures that irrigation liquid can flow all the way through during cleaning. The irrigation grooves 26 have a U-shaped cross section.

At its end lying outside the connection body 15, the latch element 20 has a head portion which has a greater diameter than the shaft portion of the latch element 20 extending into the interior of the transporter 10. The side of the head portion directed towards the shaft portion serves as a bearing surface for a spring element 24, which is designed as a metallic helical compression spring. The spring element 24 lies with its other end on a shoulder of the connection body 15 and exerts an outward pressure.

However, the latch system 18 is held in the connection body 15 of the transporter 10 by the blocking element 34. The blocking element 34 is designed substantially like the blocking element 34 shown in FIGS. 3 and 4. However, it does not engage in a complementary engagement opening but instead in a blocking groove 36, which is formed in the outer wall of the latch element 20 and of which the longitudinal axis is transverse to the longitudinal axis of the latch element 20. The blocking groove 36 is wider than the diameter of the blocking element 34, such that the desired displacement of the latch element 20 is not impeded.

Figure 6:
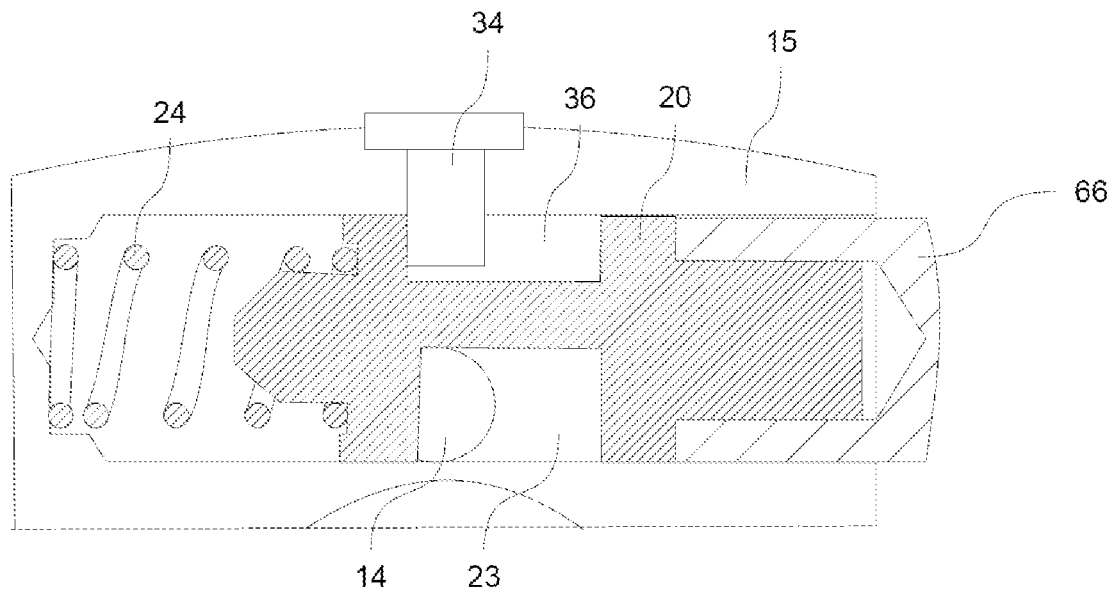
FIG. 6 shows a schematic sectional view of the latch system of an alternative transporter according to the invention, from the longitudinal direction of the transporter.

FIG. 6 shows a schematic sectional view of the latch system 18 of an alternative transporter 10 according to the invention, from the longitudinal direction of the transporter 10. In a manner not shown, the latch element 20, like the one shown in FIG. 5, comprises irrigation grooves 26 which are each suitable for forming an irrigation channel 25 between the latch element 20 and the connection body 15.

In contrast to the transporter 10 according to FIG. 5, the spring element 24 of the transporter 10 shown in FIG. 6 is arranged on that side of the latch element 20 opposite an unlatching element 66. The channel (hollow) provided in the connection body 15 for the latch element 20 is not open at both sides of the connection body 15 and is instead closed at one end. The spring element 24 is arranged on the closed side of this channel and is supported at one side on the end of the channel and at the other side on the latch element 20. To support the spring element 24, the latch element 20 has, at this end, grooves which extend about the longitudinal axis of the latch element 20 in the longitudinal direction thereof.

The unlatching element 66 is an actuation element (button) with which the latching connection between the work element 14 and the latch system 18 can be released. For this purpose, the unlatching element 66 is arranged on that side of the latch element 20 opposite the spring element 24, i.e. on the side where the channel provided for the latch element 20 in the connection body 15 is open towards the outside.

In addition, the latch system 18 shown in FIG. 6 also differs from the one shown in FIG. 5 in that the proximal end region of the work element 14 is not arranged in an engagement opening 22 of the latch element 20 but in an engagement groove 23. The engagement groove 23 is arranged in the outer wall (lateral face) of the latch element 20. The longitudinal axis of the engagement groove 23 extends transversely with respect to the longitudinal axis of the latch element 20.

The blocking element 34 has a head region which is accessible from outside the connection body 15 and which has a wider diameter than the shaft portion of the blocking element 34 arranged inside the connection body 15 and the blocking groove 36.

Although the present invention has been described in detail on the basis of the illustrative embodiments, it is obvious to a person skilled in the art that the invention is not restricted to these illustrative embodiments but rather that modifications are possible, whereby individual features can be omitted or different types of combinations of features can be implemented, without departing from the scope of protection of the accompanying claims. The present disclosure covers all combinations of the individual features shown.

LIST OF REFERENCE SIGNS

| | |
|---|---|
| 10 | transporter |
| 12 | resectoscope |
| 13 | system component |
| 14 | work instrument |
| 15 | connection body |
| 16 | shaft portion |
| 18 | latch system |
| 20 | latch element |
| 22 | engagement opening |
| 23 | engagement groove |
| 24 | spring element |
| 25 | irrigation channel |
| 26 | irrigation groove |
| 28 | end of the latch element |
| 30 | lateral transporter face |
| 32 | contralateral transporter face |
| 34 | blocking element |
| 36 | blocking groove |
| 38 | outer wall |
| 40 | irrigation channel |
| 42 | electrode instrument |
| 44 | electrode |
| 46 | shaft |
| 48 | shaft tube system |
| 50 | optics guide tube |
| 52 | guide element |
| 54 | optics |
| 56 | grip part |
| 58 | grip part |
| 60 | spring bridge |
| 62 | carriage |
| 64 | force transmission element |
| 66 | unlatching element |

The invention claimed is:

1. A resectoscope for use in endoscopic surgery, comprising:
    a transporter; and
    a system component latched in the transporter,
        wherein the transporter comprises:
            a connection body and,
            for connection to the system component, the system component being provided in the connection body,
            a latch system having an elongate latch element,
    wherein the latch element is arranged transversely with respect to a longitudinal axis of the transporter and has an engagement opening or an engagement groove, and a spring element,
    wherein one or more irrigation channels, arranged parallel to a longitudinal axis of the latch element, are formed between the latch element and the connection body,
    wherein the one or more irrigation channels have both a first end and a second end and are open to an outside of the latch element at at least one of the first end and a second end of the latch element in order to allow irrigation liquid to flush the latch element and flow to the outside of the latch element,
    wherein irrigation liquid is conveyable through the one or more irrigation channels from a lateral face of the transporter to a contralateral face of the transporter,
    wherein the latch element includes two irrigation grooves, one on each axial side of the latch element, each of the two irrigation grooves arranged parallel to the longitudinal axis of the latch element and extending toward a same longitudinal end of the latch element,
    wherein the connection body has the two irrigation grooves arranged parallel to the longitudinal axis of the latch element and adjoining the latch element, the irrigation liquid configured to be conveyed through the two irrigation grooves from the lateral face of the transporter to the contralateral face of the transporter, and
    wherein the one or more irrigation channels are formed by the two irrigation grooves and extend over an entire length of the latch element.

2. The resectoscope according to claim 1, wherein the system component has an elongate shaft portion.

3. The resectoscope according to claim 1, wherein the latch system is designed for connection to the proximal end region of the system component.

4. The resectoscope according to claim 1, wherein the proximal end region of the system component is insertable into the engagement opening or engagement groove of the latch system.

5. The resectoscope according to claim 1, wherein the system component is an electrode instrument with an elongate shaft portion and with, at its distal end, an electrode to which high-frequency current can be applied.

6. The resectoscope according to claim 5, wherein the transporter is designed to control the longitudinal displacement of the work instrument.

7. The resectoscope according to claim 1, wherein the latch system comprises an elongate blocking element which is arranged, transversely with respect to the longitudinal axis of the latch element, in a blocking groove in the outer wall of the latch element.

8. The resectoscope according to claim 1, wherein the spring element is a compression spring, preferably a helical compression spring.

* * * * *